United States Patent [19]
Dadey

[11] Patent Number: 6,063,370
[45] Date of Patent: May 16, 2000

[54] MACROMOLECULAR COMPLEXES FOR DRUG DELIVERY

[75] Inventor: Eric J. Dadey, Aurora, Ill.

[73] Assignee: The Board of Trustees of the University of Illinois, Urbana, Ill.

[21] Appl. No.: 09/155,729

[22] PCT Filed: Apr. 3, 1997

[86] PCT No.: PCT/US97/06943

§ 371 Date: Oct. 2, 1998

§ 102(e) Date: Oct. 2, 1998

[87] PCT Pub. No.: WO97/37680

PCT Pub. Date: Oct. 16, 1997

Related U.S. Application Data

[60] Provisional application No. 60/014,756, Apr. 5, 1996.

[51] Int. Cl.[7] .......................... A61K 38/28; A61K 47/32
[52] U.S. Cl. .................. 424/78.12; 424/78.1; 514/866
[58] Field of Search .................... 424/457, 78.1, 424/78.12

[56] References Cited

U.S. PATENT DOCUMENTS

| | | | |
|---|---|---|---|
| 4,489,065 | 12/1984 | Walton et al. | 424/180 |
| 4,834,965 | 5/1989 | Martani et al. | 424/488 |
| 5,443,505 | 8/1995 | Wong et al. | 623/4 |
| 5,478,575 | 12/1995 | Miyazaki et al. | 424/487 |
| 5,665,700 | 9/1997 | Cho et al. | 514/2 |

FOREIGN PATENT DOCUMENTS

| | | | |
|---|---|---|---|
| 0 424 168 A1 | 4/1991 | European Pat. Off. | A61K 47/32 |
| 862242 | 3/1961 | United Kingdom . | |

*Primary Examiner*—Peter F. Kulkosky
*Attorney, Agent, or Firm*—Marshall, O'Toole, Gerstein, Murray & Borun

[57] ABSTRACT

Novel macromolecular drug complexes containing a drug, like insulin, and a polymer having a plurality of acid moieties, like carboxyl moieties or phosphonic acid moieties, are disclosed. Compositions containing the macromolecular complexes are administered to individuals suffering from a disease, and the complexes release the drug, in vivo, to treat the disease, and to reduce, eliminate, or reverse complications associated with the disease.

31 Claims, 10 Drawing Sheets

MACROMOLECULAR COMPLEXES FOR DRUG DELIVERY

CROSS-REFERENCE TO RELATED APPLICATIONS

This application claims the benefit of provisional application Ser. No. 60/014,756, filed Apr. 5, 1996.

FIELD OF THE INVENTION

The present invention relates to macromolecular drug complexes and to the administration of the macromolecular drug complexes to individuals. More particularly, the present invention relates to a new drug delivery system comprising a macromolecular drug complex containing a therapeutic agent that is noncovalently bound, i.e., is complexed, to a polymer having a plurality of acid moieties. The complex is prepared by interacting the polymer and a therapeutic agent, such as insulin, in an aqueous medium. Depending on the physicochemical properties of the polymer and therapeutic agent, the resulting macromolecular drug complex either is water soluble or separates from the aqueous medium as a solid precipitate. The solid macromolecular complex can be incorporated into a variety of drug compositions, including solid phase drug compositions for oral administration of the therapeutic agent.

BACKGROUND OF THE INVENTION

It is well known that modern day drugs are very efficacious with respect to treating acute and chronic diseases. However, several diseases, and especially chronic diseases, are associated with complications that are not treated by administration of the drug.

Figure 1:
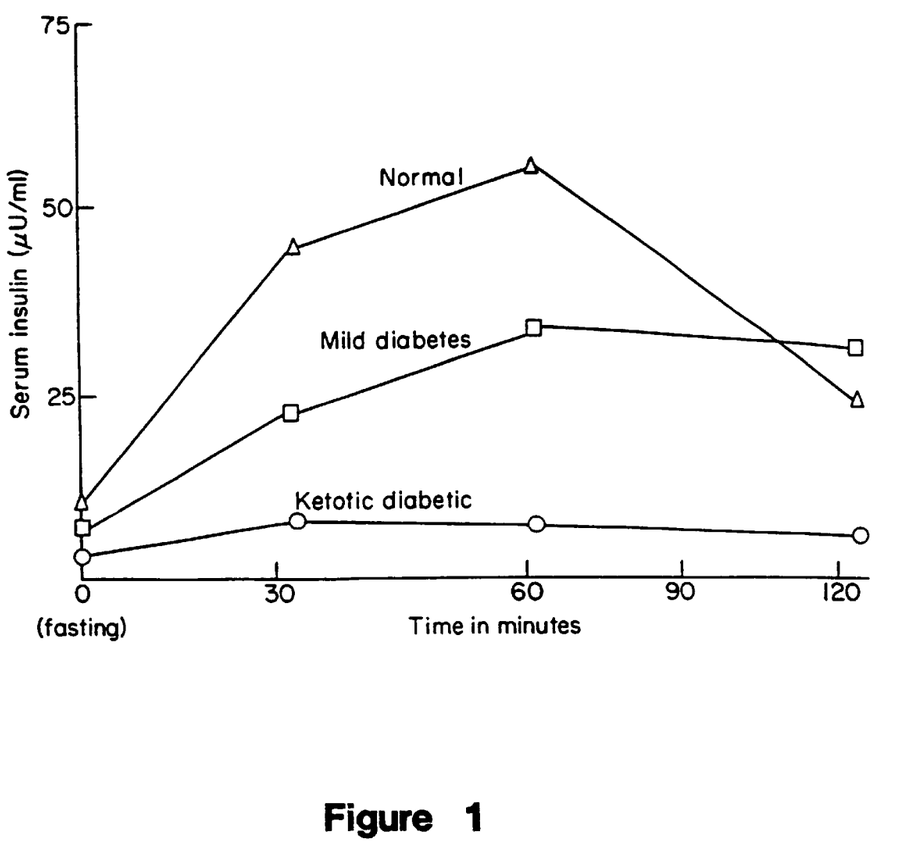
FIG. 1 is a plot showing insulin levels ($\mu$U/mL) over time (minutes) for normal individuals and diabetics.

For example, the standard treatment for diabetes is administration of insulin. An individual suffering from diabetes does not produce sufficient insulin, and hence the individual cannot burn and store glucose. Diabetes cannot be cured, but diabetes can be treated by periodic injections of insulin. FIG. 1 shows that serum insulin levels rise from a low fasting value to a peak after about 30 to 60 minutes, then fall back to a low value after about 120 minutes. In mild diabetics, the rise in serum insulin is lower compared to normal individuals. In severe diabetics, no insulin is produced, and the rise in serum insulin levels is negligible. As a result, excess glucose accumulates in the blood of a diabetic, which can result, for example, in a loss of weight and loss of strength.

However, insulin injections to treat diabetes do not treat, or alleviate, the serious vascular complications associated with diabetes, including nephropathy, retinopathy, neuropathy, heart disease, and reduced blood circulation in the limbs, i.e., "diabetic foot", that can lead to gangrene. Another disadvantage with respect to the present therapeutic compositions used to treat diabetes is that insulin must be injected. Insulin cannot be administered orally because insulin is destroyed by the strong acid conditions of the stomach.

Therefore, it would be advantageous to develop a method of both treating a disease, and preventing or reversing complications associated with the disease. It also would be advantageous to develop easier methods of administering a drug to treat the disease. As set forth in detail hereafter, the present invention is directed to novel macromolecular drug complexes, and to use of the complexes to reduce, eliminate, or reverse complications associated with a disease. The present invention is further directed to improved drug delivery systems for administering difficult to administer drugs, like insulin.

With respect to diabetes, glycosaminoglycans (GAGs) are a class of negatively charged, endogenous polysaccharides composed of repeating sugar residues (uranic acids and hexosamines). GAGs have been shown to bind a variety of biological macromolecules, including connective tissue macromolecules, plasma proteins, lysosomal enzymes, and lipoproteins. In addition, exogenous GAGs have been shown to bind to the cell surfaces of a variety of different cell types, including liver cells (hepatocytes), fibroblasts, and importantly, endothelial cells. Exogenous GAGs therefore can be internalized. Furthermore, GAGs have been implicated in the regulation of cell proliferation and in cell-cell communication, shown to interact with cell-surface receptors (cell adhesion molecules), and shown to modify the behavior of cells in culture. In addition, GAGs were shown to be highly potent, selective inhibitors of HIV replication and giant cell formation.

GAG-receptor interactions are characterized by the formation of noncolavent, self-assembling macromolecular complexes. These transient, interpolyelectrolyte complexes mediate many biological functions including enzyme-substrate binding, antigen-antibody interactions, leukocyte-endothelial cell adhesion events, drug-receptor binding, and protein-protein interactions. Furthermore, secondary binding forces, such as hydrogen bonds, van der Waals forces, and hydrophobic interactions, govern interpolyelectrolyte formation, and, ultimately, influence the resulting pharmacologic response to the complex.

G. Gambaro et al., *Kidney Int.*, 46, pages 797–806 (1994) discloses that exogenously administered GAGs have a favorable effect on morphological and functional renal abnormalities in diabetic rats, and appear to revert established diabetic renal lesions. Furthermore, D. M. Templeton, *Lab. Invest.*, 61 (2), pages 202–211 (1989) and C. W. Marano et al., *Invest. Ophthalmology Vis. Sci.*, 33 (9), pages 2619–2625 (1992) disclose that diabetic patients have a decreased glycosaminoglycan content in glomerular basement membranes. Additionally, an increase in total GAG serum levels in diabetic patients was disclosed in K. Olczyk et al., *Acta Biochimica Polonica*, 39, pages 101–105 (1992). The authors observed an increase in protein-bound GAGs, such as keratan sulfate, hyaluronic acid, heparin sulfate, and heparin in diabetic patients. Gambaro et al. also discloses an increase in the urinary excretion rate of GAGs from insulin-dependent diabetic patients.

Therefore, publications show that glycosaminoglycans play an important, yet unexplained, role in the vascular changes associated with lifelong insulin therapy. In particular, administration of GAGs to diabetic animals has inhibited or reversed some vascular abnormalities. The publications also strongly suggest that exogenous insulin plays a role in elevating the level of GAGs in the urine and serum of diabetic patients. Furthermore, the publications clearly show that glycosaminoglycans bind to a multitude of biological macromolecules, including proteins.

These observations appear to suggest utilizing glycosaminoglycans as an adjuvant to insulin therapy. However, GAGs are anticoagulants and long term use of GAGs with insulin would thin the blood of an individual to unacceptable levels. Furthermore, the risks associated with a long term use of GAGs are unknown. In addition, GAGs are heterogeneous, having a relatively wide molecular weight range of about 8,000 to about 20,000, and accordingly are difficult to reproduce. Therefore, although persons skilled in the art have used GAGs as therapeutic agents, e.g., heparin, GAGs have not been used for extended periods of time, or for the treatment of a chronic disease, like diabetes. The present invention is directed to finding drug complexes that provide the benefits of an insulin-GAGs complex, but that avoid the disadvantages associated with long term administration of a GAG compound.

SUMMARY OF THE INVENTION

The present invention is directed to a novel drug delivery system, wherein a drug is complexed with a polymer having a plurality of acid moieties. The macromolecular complexes treat the underlying disease, e.g., insulin to treat diabetes, and complications associated with the disease, e.g., prevent or reverse the vascular problems associated with diabetes. The present macromolecular drug complexes can be water soluble or water insoluble at neutral pH. Therefore, the macromolecular drug complex can be administered in a variety of dosage forms.

More particularly, the present invention is directed to a macromolecular drug complex containing a drug and a polymer having a plurality of acid moieties and a weight average molecular weight ($M_w$) of about 1,000 to about 50,000. In accordance with an important aspect of the present invention, the drug contains at least one quaternary ammonium nitrogen atom for binding to, and complexing with, the polymer. Preferred drugs are polypeptides or proteins. The polymer contains a plurality of acid moieties for complexing with the drug. The acid moiety can be a carboxyl group, sulfate group, sulfonate group, phosphonic acid group, phosphoric acid group, phenolic group, or a similar acid moiety.

Another aspect of the present invention is to provide a macromolecular drug complex wherein the polymer is a naturally-occurring polymer or a synthetic polymer.

Another aspect of the present invention is to provide a macromolecular drug complex containing a drug and a polymer in a weight ratio of drug to polymer of about 10 to about 90 to about 90 to about 10.

Yet another aspect of the present invention is to provide a water-soluble macromolecular drug complex containing a drug and a salt form of the polymer, wherein the complex can be administered to an individual in a liquid form.

Still another aspect of the present invention is to provide a water insoluble macromolecular drug complex containing a drug and the free acid form of the polymer, wherein the complex can be administered to an individual in a solid form. Such a macromolecular drug complex is especially useful for oral administration of a drug to an individual.

Another aspect of the present invention is to provide a macromolecular drug complex that can be administered to an individual to treat an acute or chronic disease and to alleviate, eliminate, or reverse complications associated with the disease.

Another aspect of the present invention is to provide macromolecular drug complexes that remain intact and do not dissociate immediately after administration, and that are capable of releasing the drug in vivo to treat a disease.

Still another aspect of the present invention is to provide a macromolecular drug complex wherein the drug is insulin, methotrexate, isoniazid, chloroquine phosphate, a polypeptide, or a protein.

Another aspect of the present invention is to provide a macromolecular drug complex containing insulin and a polymer selected from the group consisting of polyacrylic acid and polyvinylphosphonic acid.

Yet another aspect of the present invention is to provide a macromolecular insulin complex that treats diabetes and that prevents, alleviates, or reverses vascular complications that are associated with diabetes and that are left unchecked by conventional insulin formulations.

One other aspect of the present invention is to provide alternate routes of administration for the safe, easy, and effective delivery of insulin, especially to provide an oral route of administration for insulin.

These and other novel features and aspects of the present invention will become apparent from the following detailed description of the preferred embodiments.

DETAILED DESCRIPTION OF THE PREFERRED EMBODIMENTS

It is well known that a wide range of biological functions are mediated by the formation of noncovalent, macromolecular complexes. Examples include enzyme-substrate binding, antigen-antibody interactions, leukocyte-endothelial cell adhesion events, drug-receptor binding, and protein-protein interactions. However, utilization of these self assembling complexes as drug delivery systems is new and uninvestigated.

The present application discloses a novel drug delivery system which utilizes a macromolecular drug complex containing a drug and a naturally-occurring or synthetic polymer. The macromolecular drug complex is useful for the oral, parenteral, sublingual, transdermal, conjunctival, intraocular, intranasal, aural, intrarespiratory, rectal, vaginal, or urethral delivery of therapeutic agents. The therapeutic agent can be, for example, but not limited to, peptides, proteins, antibacterials, antifungals, antineoplastics, antiprotozoals, antiarthritics, and antiinflammatory agents. In a preferred embodiment, the therapeutic agent is a polypeptide or a protein. In especially preferred embodiments, the therapeutic agent is insulin.

As will be discussed in detail hereafter, the physicochemical properties of the present macromolecular complexes were investigated. The interactions of insulin with polymers were monitored using multi-angle laser-light scattering (MALLS) and turbidimetry, and by potentiometric titration. Formation of a white, fluffy precipitate, and other evidence, confirmed the presence of the macromolecular insulin complexes. Turbidimetric analysis of an aqueous suspension of the complex indicated that the physicochemical properties of the complex vary with the initial complexing conditions. Furthermore, light scattering data indicated that complexation could involve the initial formation of a kinetically, and a subsequent thermodynamically, favored complex. Preliminary solubility studies show that the macromolecular drug complex is well suited for oral delivery of therapeutic agents.

The following discussion is particularly directed to macromolecular drug complexes including the drug insulin. However, persons skilled in the art are aware that other drugs having the structural characteristics of insulin, especially other polypeptide and protein therapeutic agents, similarly can be complexed with a polymer having a plurality of acid moieties, to provide a macromolecular drug complex of the present invention.

As previously discussed, a drug, like insulin, can treat and control a disease, like diabetes, but cannot prevent, attenuate, or rectify complications associated with the disease, such as vascular problems, like heart disease and "diabetic foot". Therefore, it would be advantageous to administer insulin to a diabetic in a form that not only treats the disease, but also prevents, alleviates, or reverses complications associated with the disease.

An important additional advantage would be to provide a method of administering a drug, like insulin, orally. Insulin, and other drugs, and especially many protein and polypeptide based drugs, cannot be administered orally because the drug is altered in the stomach, and therefore is unavailable to the body in a form to combat or control a disease.

With respect to diabetes, it is known that glucose can complex with proteins to produce toxic by-products. Such toxic by-products have been theorized as the cause of the complications associated with diabetes. It also has been observed that diabetics have elevated levels of GAGs in serum and urine, and a lower GAG content in their kidney cell membranes. It also is known that administration of GAGs to diabetic animals inhibited and/or reversed some vascular abnormalities associated with diabetes. Diabetics also have altered blood chemistries, including elevated levels of various enzymes in addition to glucose.

Therefore, the following has been hypothesized, but is not relied upon, as a cause for the complications associated with diabetes. In particular, the interior of vascular walls are lined with endothelial cells. Branching from the endothelial cells are proteoglycan molecules. Glucose is able to bond with these surfaces of the endothelial cells. However, GAGs also are known to be present on the proteglycan branches on the surface of endothelial cells. In addition, insulin also is known to have the capability to complex with the GAG compounds. It is hypothesized, therefore, that insulin complexes with the GAGs present on the branches of the endothelial cells, and that the GAGs-insulin complexes are removed from the cell by enzymatic activity, thereby leaving the surfaces endothelial cells devoid of GAGs compounds.

An increased insulin dosage provides sufficient insulin to account for the insulin lost as a result of the insulin-GAGs interaction. But the sloughing of GAGs from endothelial cells exposes the vascular surface to numerous unwanted reactions, including repeated glycosylation. Repeated glycosylation can be exacerbated by the naturally elevated levels of serum glucose in a diabetic. Therefore, it has been found that the interaction between insulin and the GAGs on the endothelial cells can be circumvented by complexing insulin such that the insulin is unavailable to interact with the GAGs on the surface of endothelial cells.

Since the present investigators have found evidence of a GAGs complex with insulin, the present investigators considered complexing insulin with a GAG, and thereby protect vascular endothelial cells from the harmful effects of constant exposure to insulin. Then, the insulin would not be available to complex with GAGs on the surface of endothelial cells. As a result, the endothelial cells would not be vulnerable to glycosylation as a result of a sloughing off of the GAGs-insulin complex.

However, GAGs are well known anticoagulants and their long term effects on a diabetic are unknown. As a result, a GAG could not be administered to an individual on a long term basis because, for example, the blood of the individuals would be thinned too greatly.

In accordance with the present invention, it has been shown that insulin, and other drugs, can be complexed with suitable naturally-occurring and synthetic polymers, to provide a macromolecular drug complex that avoids the interaction between insulin and a GAG on the surface of an endothelial cell. It is hypothesized that the vascular endothelial cells therefore are spared from undesirable reactions, like glycosylation, and vascular complications associated with diabetes can be eliminated or attenuated. Furthermore, the present macromolecular drug complexes make the insulin available to the individual, such that diabetes is controlled. Similarly, other drugs, in addition to insulin, can be complexed, and are available to treat the disease of concern.

The use of a suitable naturally occurring or synthetic polymer also avoids the harmful side effects of GAGs (e.g., anticoagulation), and insures the quality, reproducibility, and uniformity of the macromolecular drug complex because the polymers have a reproducible chemical makeup, and the molecular weight can be controlled. Furthermore, by a proper selection of a polymer, the in vivo behavior of insulin can be controlled to optimize the pharmacologic response of insulin, and the route of administration can be regulated.

The drug present in the macromolecular drug complex can be any drug capable of complexing with an acid moiety. Typically, the drug has at least one positively charged site. The positively charged site usually is a quaternary ammonium nitrogen atom. The drug can be a naturally occurring or synthetic drug. The drug can be monomeric, or oligomeric or polymeric, like a polypeptide or protein. Preferred drugs are polypeptide or protein based.

If the drug is a synthetic drug, the drug often contains a nitrogen atom that can be quaternized. If the drug is a naturally occurring drug, the drug often contains an amino acid having a positively charged site. These quaternized nitrogen atoms and positively charged sites are available to complex with the acid moieties of the polymer.

For example, if the drug is insulin, insulin contains fifty-one amino acids in two polypeptide chains. The insulin molecule contains the amino acids lysine, arginine, and histidine. Each of these amino acids has a positively charged site, thereby permitting insulin to complex with the polymer through the acid moieties of the polymer.

Other drugs that can be complexed with a polymer having a plurality of acid moieties to form a macromolecular drug complex of the present invention include, but are not limited to, anti-inflammatory drugs, like tereofenamate, proglumetacin, tiaramide, apazone, benzpiperylon, pipebuzone, ramifenazone, and methotrexate; anti-infective drugs, like isoniazid, polymyxin, bacitracin, tuberactionomycin, and ethryomycin; anti-arthritis durgs, like penicillamine, chloroquine phosphate, glucosamine, and hydroxychloroquine; diabetes drugs, like insulin, and glucagon; and anti-cancer drugs, like cyclophosphamide, interferon α, interferon β, interferon γ, vincristine, and vinblastine.

The polymer used to prepare the macromolecular drug complex has a plurality of acid moieties. Any physiologically acceptable polymer can be used as long as the polymer contains sufficient acid moieties to complex with the drug. Typically, the polymer has sufficient acid moieties if the polymer can be solubilized in water by neutralizing the polymer with a base. Such polymers are prepared from a monomer, or mixture of monomers, wherein at least 25% of the monomers, by weight of the polymer, contain an acid moiety. Preferably, at least 40% of the monomers, by weight of the polymer, contain an acid moiety. To achieve the full advantage of the present invention, at least 60% of the monomers, by weight of the polymer, contain an acid moiety. If the polymer is a homopolymer, the monomers containing an acid moiety can be 100% by weight of the polymer. By proper selection of the polymer, persons skilled in the art are able to regulate the pharmacologic response of the drug and the route of administration of the drug.

The polymer can be a synthetic polymer or a naturally occurring polymer. In general, the polymer has an $M_w$ of about 1,000 to about 50,000 and preferably about 2,000 to about 20,000. To achieve the full advantage of the present invention, the polymer has an $M_w$ of about 4,000 to about 15,000.

With respect to synthetic polymers, preferred polymers are linear polymers. However, lightly cross-linked polymers also can be used. A lightly crosslinked polymer has one to about five crosslinks crosslinking the linear chains of the polymer molecule and is soluble in water. An important feature of the polymer is that the polymer is water soluble, and contains acid moieties, such as carboxyl, phosphate, phosphonate, sulfate, sulfonate, phenolic, or any other moiety having a labile hydrogen that can be removed from the moiety to provide a negatively charged site on the polymer.

The polymer typically is an acrylic polymer containing a sufficient amount of acid-containing monomers, like acrylic acid, methacrylic acid, or vinylphosphonic acid. The acid-containing monomer can be, but is not limited to, acrylic acid, methacrylic acid, maleic acid, fumaric acid, itaconic acid, mesaconic acid, citraconic acid, vinylphosphonic acid, and similar α, β-unsaturated carboxylic acids and α, β-unsaturated dicarboxylic acids.

The polymer can be a homopolymer of an acid-containing monomers, like α, β-unsaturated carboxylic acids, or can be a copolymer. For example, a suitable copolymer can be an acid-containing monomer that is copolymerized with ethylene, propylene, or a similar $C_4$–$C_5$ alkene, or a $C_1$–$C_{12}$ ester of an α, β-unsaturated carboxylic acid, vinyl propionate, acrylamide, or methacrylamide, or that is copolymerized with an aromatic monomer, like styrene, α-methyl toluene, or vinyl toluene. Other comonomers include vinylpyrrolidone, vinyl alcohol, vinyl acetate, and vinyl alkyl ethers.

Examples of polymers include, but are not limited to, polyacrylic acid, polyvinylphosphonic acid, polyvinylsulfonic acid, polystyrenesulfonic acid, polymaleic acid, polymethacrylic acid, polyvinylsulfuric acid, poly(2-methacroyloxyethane-1-sulfonic acid, poly(4-vinylbenzoic acid), poly(3-(vinyloxy)propane-1-sulfonic acid), poly(3-(vinyloxy)propane-1-sulfonic acid), poly(3-methacryloxypropane-1-sulfonic acid), polymethacrylic acid, poly(4-vinylphenol), poly (4-vinylphenyl sulfuric acid), and poly(N-vinylsuccinamidic acid). In other embodiments, a polymer containing an aromatic monomer can be sulfonated or sulfated to position acid groups on the aromatic monomer. Preferred polymers are polyacrylic acid and polyvinylphosphonic acid.

With respect to naturally-occurring polymers, the above-discussed disadvantages resulting from using a GAG limits the naturally-occurring polymers to those that do not adversely effect an individual over the long term, i.e., a strong anticoagulant should not be used as the polymer. However, GAGs that act as anticoagulants have a relatively high molecular weight of about 12,000 or greater. Therefore, analogs of GAGs that do not act as strong anticoagulants can be used as the polymer. Such polymers have a structure that is similar to a GAG compound, but have a lower $M_w$, i.e., less than about 12,000.

Therefore, useful naturally-occurring polymers have an $M_w$ of about 1,000 to about 12,000, and preferably about 2,000 to about 8,000, and do not act as coagulants at the level they are administered in the macromolecular drug complex, i.e., about 2 mg/day. This dose is less than the 20 mg/day dose required to observe anticoagulation effects and therefore mild anticogulants can be used as the polymer. Furthermore, the low $M_w$, naturally occurring polymers have a greater bioavailability. For example, heparin having an $M_w$ of about 6,000 is 85% bioavailable, but as the $M_w$ increases, bioavailability decreases exponentially. Suitable naturally occurring polymers therefore include, but are not limited to, heparin, dermatan sulfate, chondroitin sulfate, keratan sulfate, heparan sulfate, hyaluronic acid, the various forms of carrageenan, and mixtures thereof, having a molecular weight ($M_w$) of about 1,000 to about 12,000. Overall, a synthetic polymer is preferred over a naturally-occurring polymer because synthetic polymers are more uniform chemically, and a desired $M_w$ is more easily achieved.

To illustrate the ability of a drug to form a macromolecular drug complex with a polymer having a plurality of acid moieties, an aqueous insulin solution was admixed with an aqueous solution of polyvinylphosphonic acid. In this experiment, a stock solution of insulin, available from Sigma Chemical Co., St. Louis, Mo., was prepared at a known concentration and varying amounts polyvinylphosphonic acid, available from Polysciences, Inc., Warrington, Pa., were added to the insulin. Macromolecular insulin complex formation was detected visually by the appearance of a white, fluffy precipitate and quantified by turbidimetric measurements.

In addition to insulin, macromolecular drug complexes were prepared in an identical manner using the drugs methotrexate, isoniazid, and chloroquine phosphate. Other macromolecular drug complexes were prepared using polyacrylic acid as the polymer.

Figure 2:
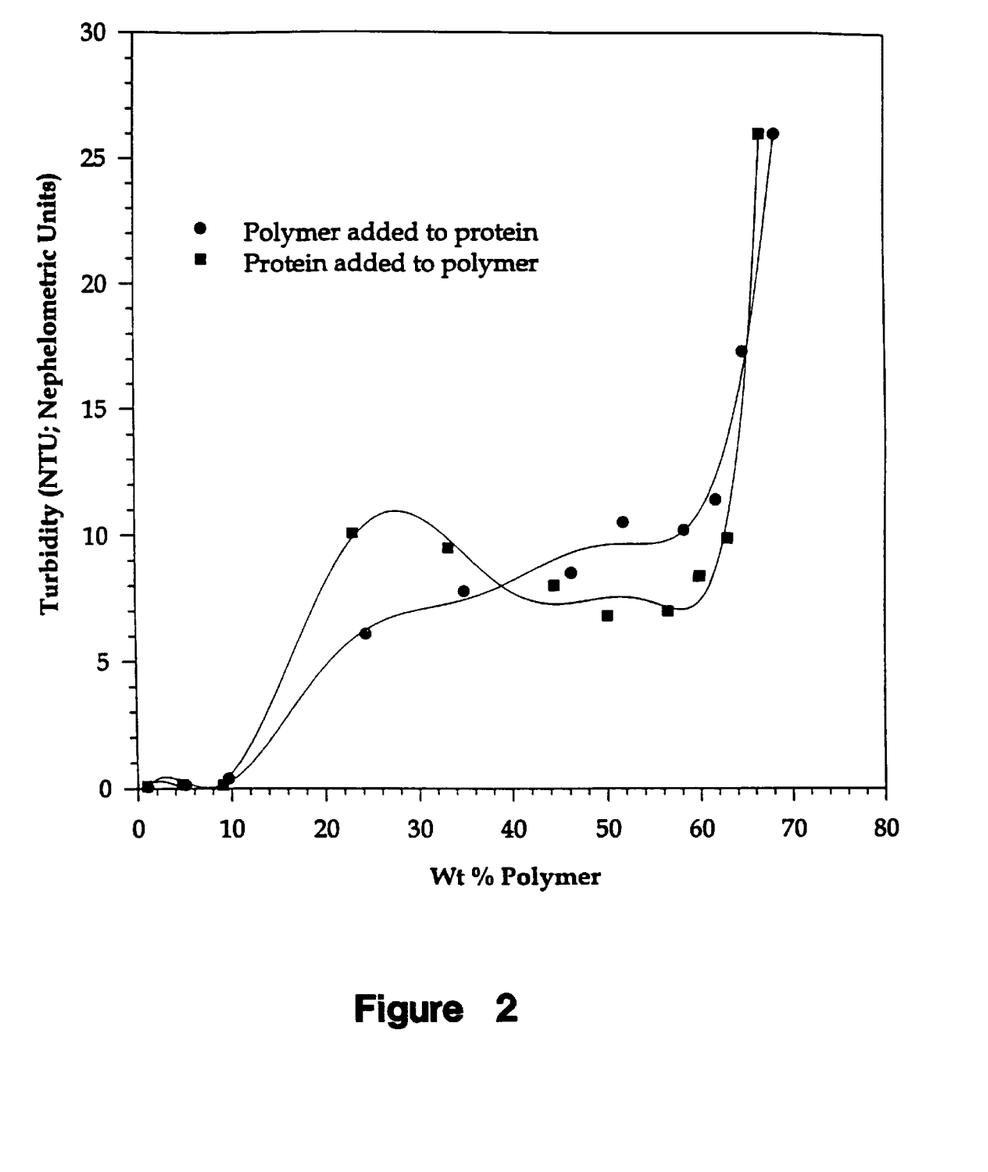
FIG. 2 are plots of turbidity (NTU) vs. weight % polymer in the complex for mixtures of 1.0 mg/mL insulin solution with various amounts of polyvinylphosphonic acid, both for polymer added to the insulin and for insulin added to the polymer.

FIG. 2 shows the effect of polymer addition to a solution containing 1.0 mg/mL insulin on the turbidity of the resulting mixture. An increase in the turbidity of the mixture as polymer is added to an insulin solutions shows complex formation. FIG. 2 shows formation of the complex (i.e., the solution becomes turbid) with the addition of 22% polymer, by weight of polymer and insulin.

Figure 3:
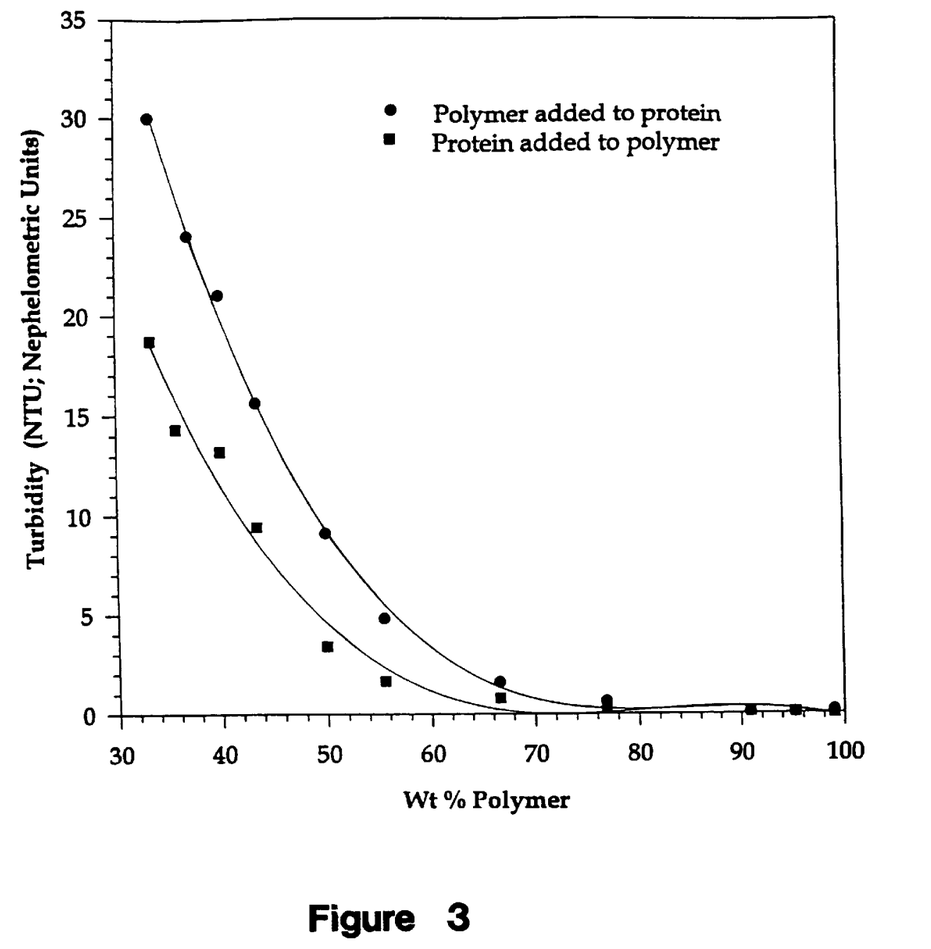
FIG. 3 are plots of turbidity (NTU) vs. weight % polymer in the complex for mixtures of 1.0 mg/mL polyvinylphosphonic acid with various amounts of insulin, both for polymer added to the insulin, and for insulin added to the polymer.
Figure 4:
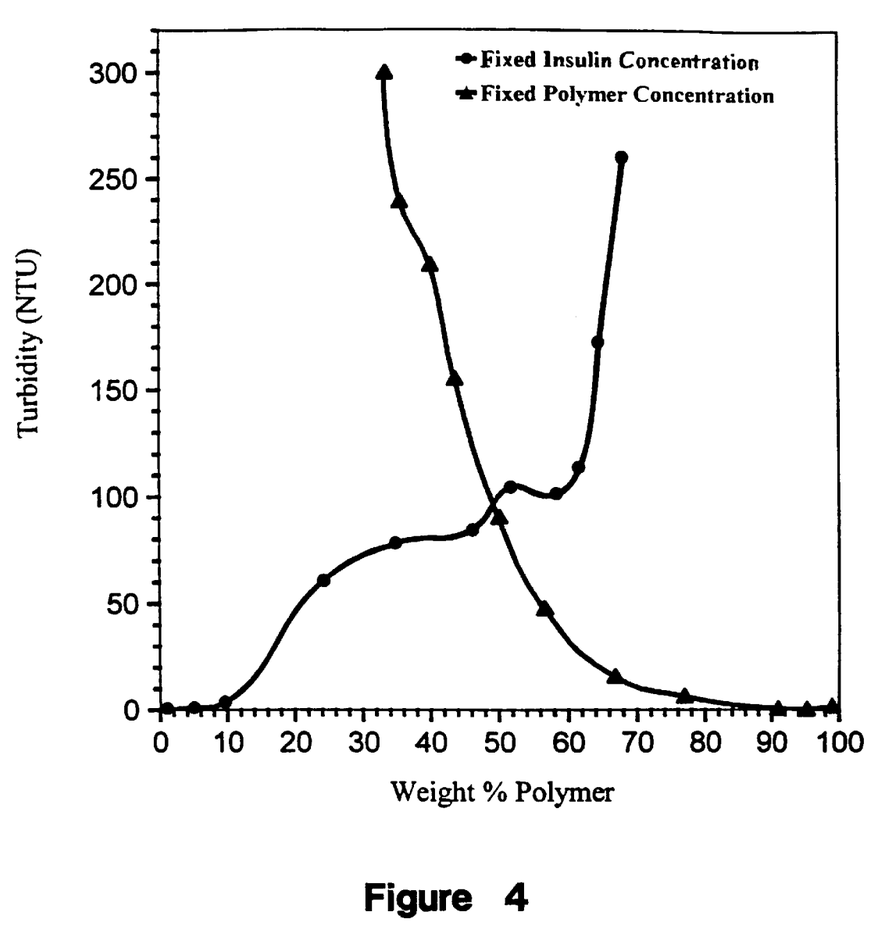
FIG. 4 are plots of turbidity (NTU) vs. weight % polymer in the complex summarizing and combining the plots of FIGS. 2 and 3.

However, when the polymer concentration is fixed at 1.0 mg/mL, and varying amounts of insulin are combined with the polymer, different results are observed, as illustrated in FIG. 3. In FIG. 3, an increase in turbidity again is indicative of complex formation. The plots of FIG. 3 show that complex formation was detected at low levels of polymer, but higher polymer concentrations produced a clear solution. The plots in FIGS. 2 and 3 show that complex formation is dependent upon several factors, including the order of addition of the drug and polymer and the weight ratio of the drug to the polymer. FIG. 4 combines the plots of FIGS. 2 and 3 to more clearly show the variables with respect to forming a macromolecular drug complex.

In particular, further tests showed that complex formation is optimized by adding the polymer to the drug, and by using minimal agitation or stirring to mix the reactants. Good complex formation however was observed when the drug was added to the polymer with minimal or no agitation or stirring.

To confirm formation of a macromolecular drug complex, a technique to determine the molecular weight of polymers in solution, termed continuous-flow multi-angle laser-light scattering (CF-MALLS), was developed. The CF-MALLS technique makes a molecular weight determination quickly without using chromatography and with little or no sample preparation. In particular, a refractive index (RI) detector (Waters 410, Waters Corp, Cambridge, Mass.) was connected in series to a light scattering (LS) detector (MiniDawn Multi-Angle Laser Light Scattering Detector, Wyatt Technologies, Santa Barbara, Calif.) and a continuous flow multistatic pump. Simply continuously circulating a solution through the detectors permits measurement of the polymer molecular weight in solution.

The CF-MALLS technique was performed on polymers of known molecular weight, and provided excellent correlation between experimental results and known molecular weights. The results are summarized in Table 1 below.

MOLECULAR WEIGHT ANALYSIS OF POLYMER STANDARDS AND INSULIN/POLYMER COMPLEXES BY CONTINUOUS-FLOW MULTI-ANGLE LASER-LIGHT SCATTERING AND BY GAS PHASE CHROMATOGRAPHY (GPC)

| POLYMER | $M_w$(g/mol) (GPC) | $M_w$(g/mol) (CF-MALLS) |
|---|---|---|
| Pullulan Standard | 12,200 | 12,232 ± 300 |
| Dextran | 36,000 | 34,680 ± 200 |
| Bovine Serum Albumin | 66,450 | 67,854 ± 400 |
| Dextran | 72,000 | 69,970 ± 300 |
| Pullulan Standard | 380,000 | 285,525 ± 250 |
| Insulin | 6,000 | 9,045 ± 200 |
| PVPA | 5,000 | 4,015 ± 30 |
| PVPA/Insulin (30:70 by weight) | | 30,470–59,460 |
| PVPS/Insulin (50:50 by weight) | | 162,100–218,100 |
| PVPA/Insulin (90:10 by weight) | | 40,010–371,400 |

1. Polyvinylphosphonic acid;
2. The first value represents the $M_w$ of the complex immediately after admixing the insulin polymer, the second value represents the $M_w$ at a later time, i.e., real-time complex formation.

Figure 5:
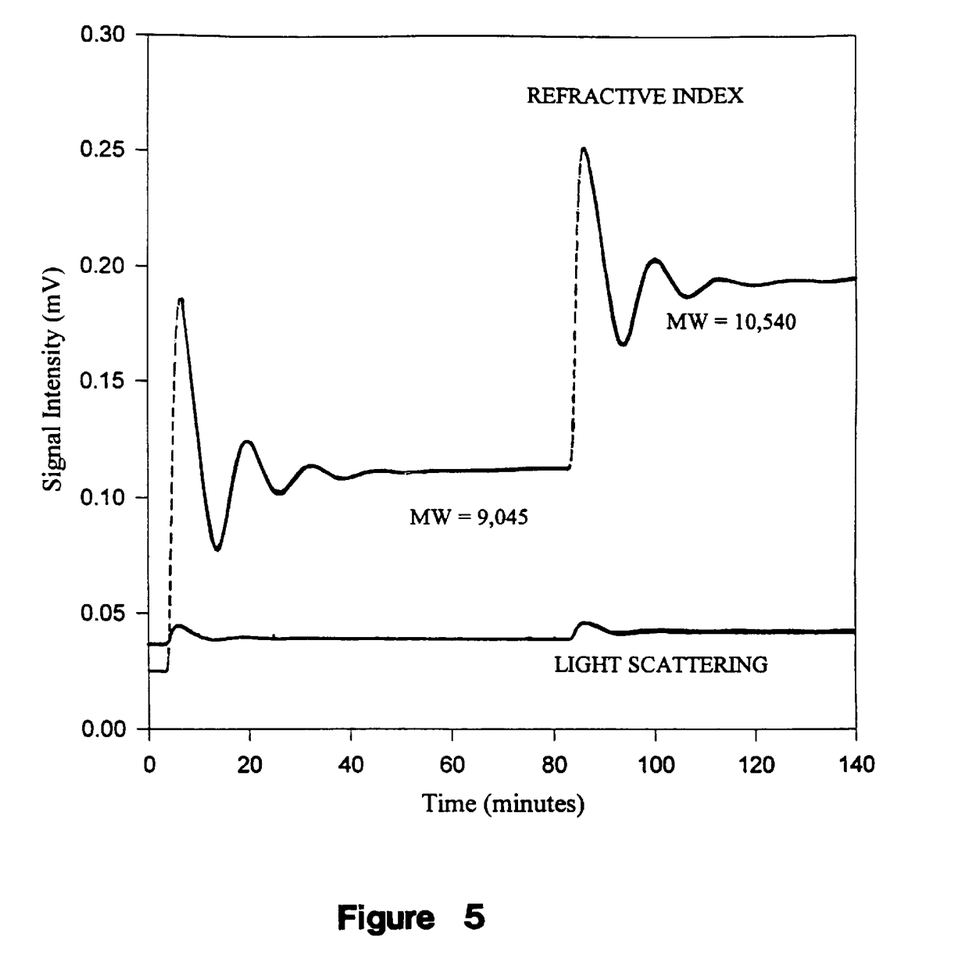
FIG. 5 are plots of refractive index (RI) and light scattering (LS) signal intensities (mV) vs. time (minutes) for two 300 mg aliquots of insulin.

The CF-MALLS technique also illustrates formation of the macromolecular drug complex over time. FIG. 5 shows an analysis of insulin using the CF-MALLS technique. Adding insulin to an aqueous medium, in 300 mg aliquots, at time zero and again about 87 minutes, shows that the RI and LS detectors yield equivalent signal intensities for each addition of insulin, i.e., the detectors merely detected an increase in the concentration of insulin, not an increase in $M_w$. The $M_w$ values were calculated from Rayleigh's equation after each insulin addition. The $M_w$ values were about 9,000 g/mol and about 10,540 g/mol. The known $M_w$ of insulin is about 6,000 g/mol. The increased $M_w$ is attributed to physical entanglements of insulin molecules, which, as expected, increase as the insulin concentration in increases.

Figure 6:
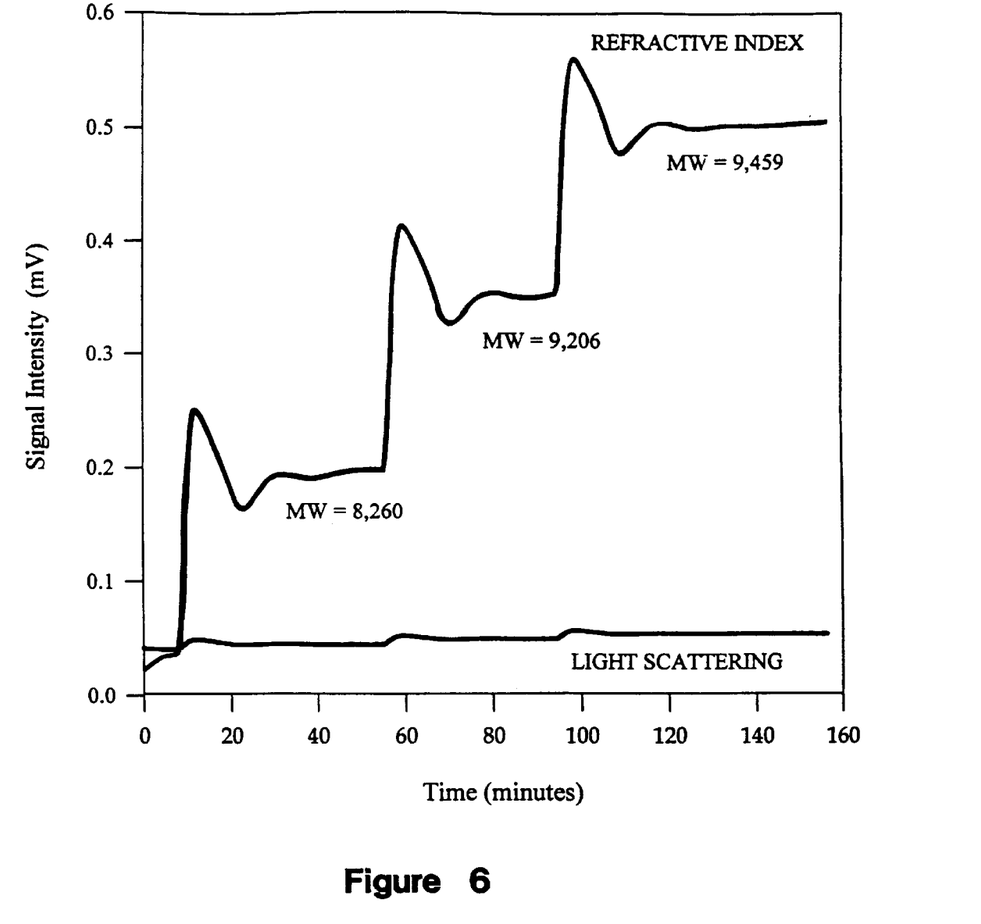
FIG. 6 are plots of refractive index (RI) and light scattering (LS) signal intensities (mV) vs. time (minutes) for three 300 mg samples of polyvinylphosphonic acid.

FIG. 6 shows a similar analysis for polyvinylphosphonic acid after three separate additions of 300 mg of polyvinylphosphonic acid to an aqueous medium at time zero, at about 60 minutes, and at about 100 minutes. Like insulin, the RI and LS detectors show equivalent signal intensities for each addition of polyvinylphosphonic acid, i.e., the detectors detected an increase in the concentration of polyvinylphosphonic acid. The test also allowed determination of the $M_w$ of polyvinylphosphonic acid after each addition, i.e., 8,260, 9,206, and 9,459 g/mol, respectively. The $M_w$ of pure polyvinylphosphonic acid is 4,051 g/mol. However, like insulin, the apparent $M_w$ of polyvinylphosphonic acid is greater in aqueous solution because of dimerization, and physical interactions, like chain entanglements, which increase with increasing polymer concentration. The $M_w$ again was calculated using Rayleigh's equation after each polymer addition.

Figure 7:
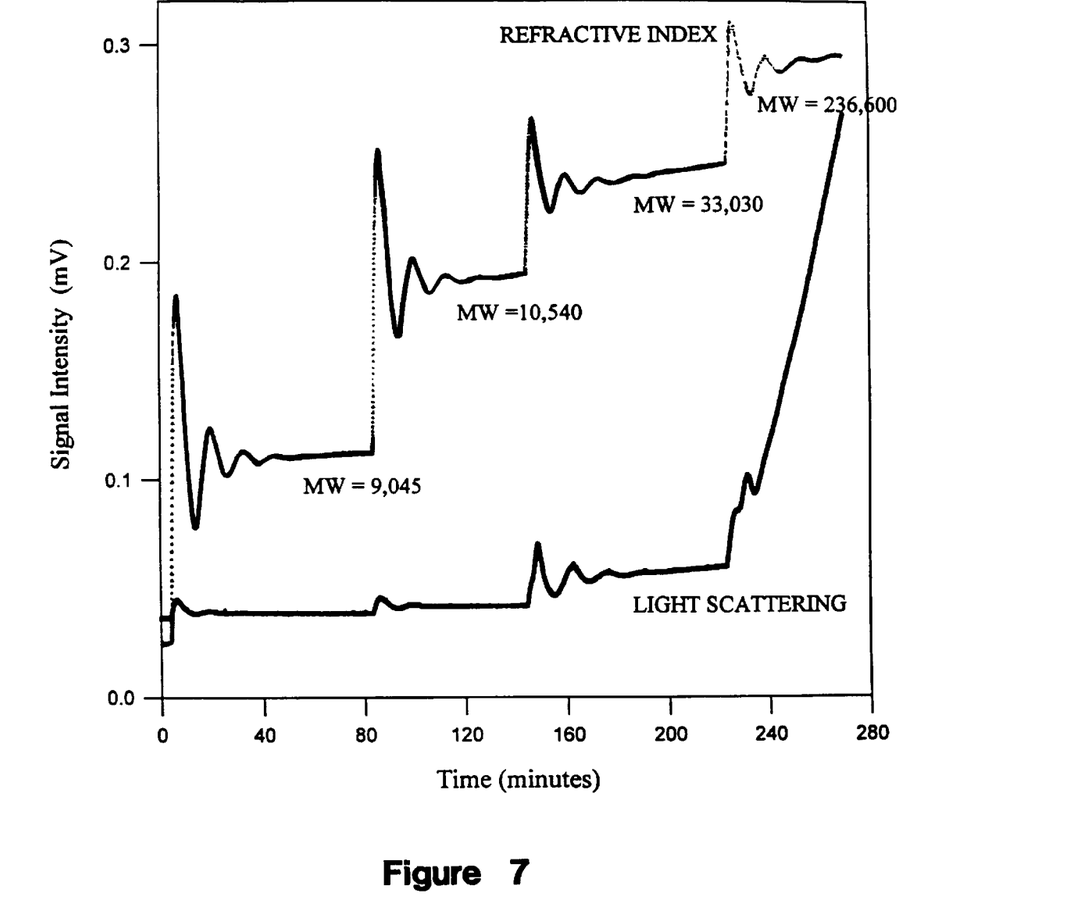
FIG. 7 are plots of refractive index (RI) and light scattering (LS) signal intensities (mV) vs. time (minutes) for the addition of polyvinylphosphonic acid to insulin.

FIG. 7 shows complex formation between insulin and polyvinylphosphonic acid. In this test, insulin (300 mg aliquots) were added to an aqueous medium at time zero and after 87 minutes. The results were identical to the results in FIG. 5. However, a subsequent addition of two 300 mg portions of polyvinylphosphonic acid to the resulting insulin solution at 160 minutes and 240 minutes produced a lower increase in RI than expected from FIG. 6, and a disproportionately greater increase in the LS signal than expected from FIG. 6.

Although the molecular weight of pure polyvinylphosphonic acid is 4051 g/mol, the $M_w$ of the resulting macromolecular drug complex increased to 33,030 g/mol at 220 minutes. The subsequent addition of an additional 300 mg of polyvinylphosphonic acid resulted in a macromolecular drug complex having an initial $M_w$ of 162,100 g/mol, which rapidly increased to 236,600 g/mol at 265 minutes. Accordingly, the large increase in $M_w$ after the first addition of polyvinylphosphonic acid, and the exponential increase in $M_w$ after the second addition of polyvinylphosphonic acid, demonstrated that a macromolecular drug complex was formed.

In addition to demonstrating that a macromolecular drug complex can be formed, it also was demonstrated that the complex has the ability to release the drug in vivo to treat a disease. In particular, a series of in vivo studies were performed to evaluate the effect of the macromolecular drug complex on serum glucose levels in normal, adult male, New Zealand white rabbits. In these studies, a rabbit, weighing three to five kilograms, was fasted overnight. Prior to dosing, the ears of the rabbit were shaved and anesthetized with a topical cream (i.e., Emla cream). A 22 gauge catheter was inserted into the left marginal ear vein, and a 0.50 mL blood sample withdrawn to establish basal serum glucose levels. A 0.050 units/Kg bolus dose of either insulin or a macromolecular insulin complex was injected into the right marginal ear vein, and 0.50 mL blood samples were withdrawn every 10 minutes for the first hour, every 20 minutes for the second hour, and every 30 minutes for the third hour post dosing. Serum glucose levels were determined utilizing standard glucose assays. Approximately 50 μL of blood was assayed immediately after sampling using a One Touch Glucometer, available from LifeScan, Inc., and the remainder of the sample was analyzed by a standard glucose colorimetric assay, available from Sigma Diagnostics, as Assay # DA510. The results are illustrated in FIGS. 8 and 9.

Figure 8:
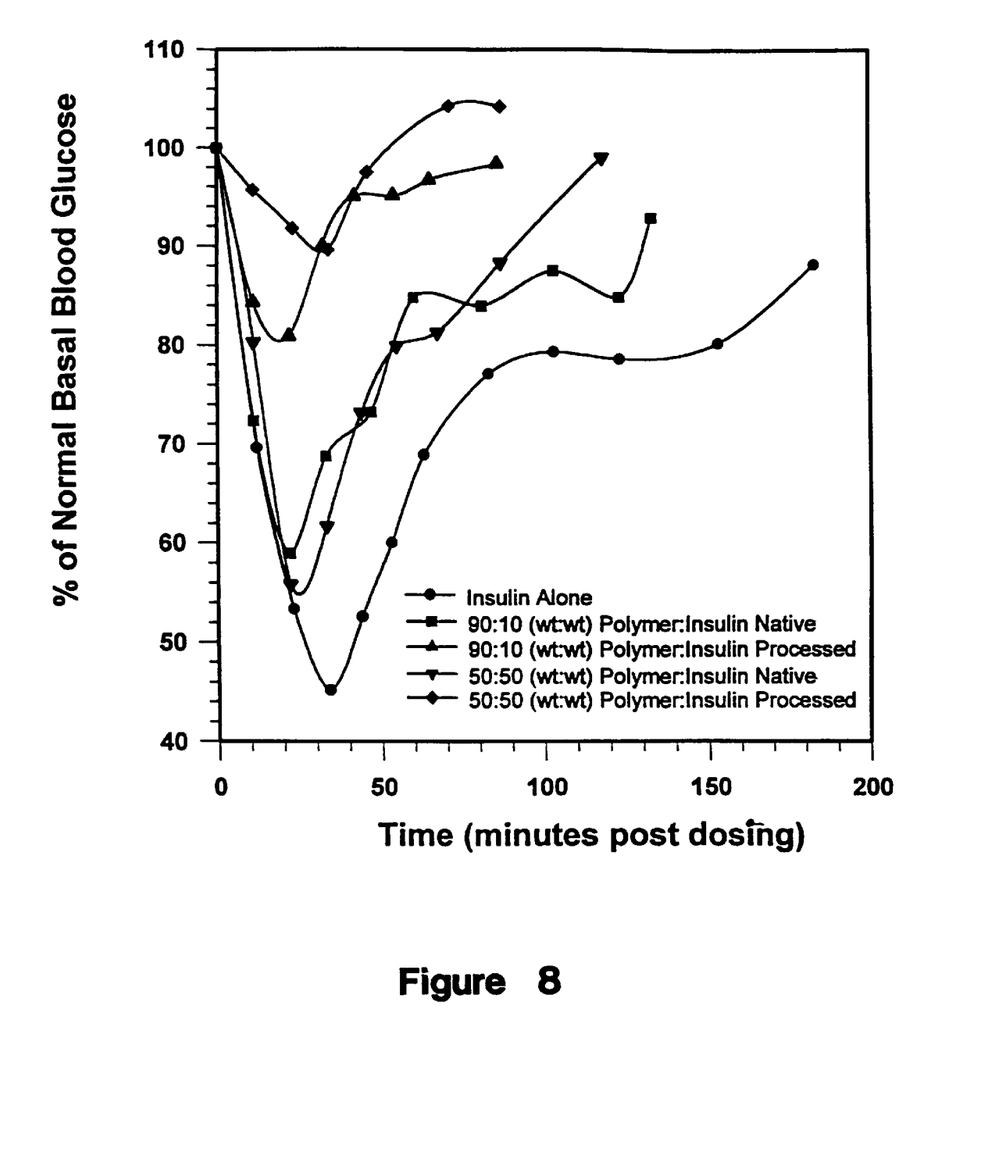
FIGS. 8 and 9 are plots of % normal blood glucose vs. time for male rabbits administered either uncomplexed insulin or a macromolecular drug complex containing insulin and polyvinylphosphonic acid.

As illustrated in FIG. 8, uncomplexed insulin was compared to macromolecular insulin complexes at an insulin dose of 0.050 units/Kg. The macromolecular insulin complexes containing 90% polymer and 10% insulin (90:10, wt/wt) were prepared by mixing aqueous solutions of insulin and polyvinylphosphonic acid (i.e., native insulin), or by mixing the compounds and then subjecting the complex to low levels of shear (i.e., processed insulin). Similar native and processed complexes containing 50:50 wt/wt insulin and polymer also were prepared. The complexes were administered to fasted, adult male rats, and serum glucose levels were assayed periodically.

Figure 9:
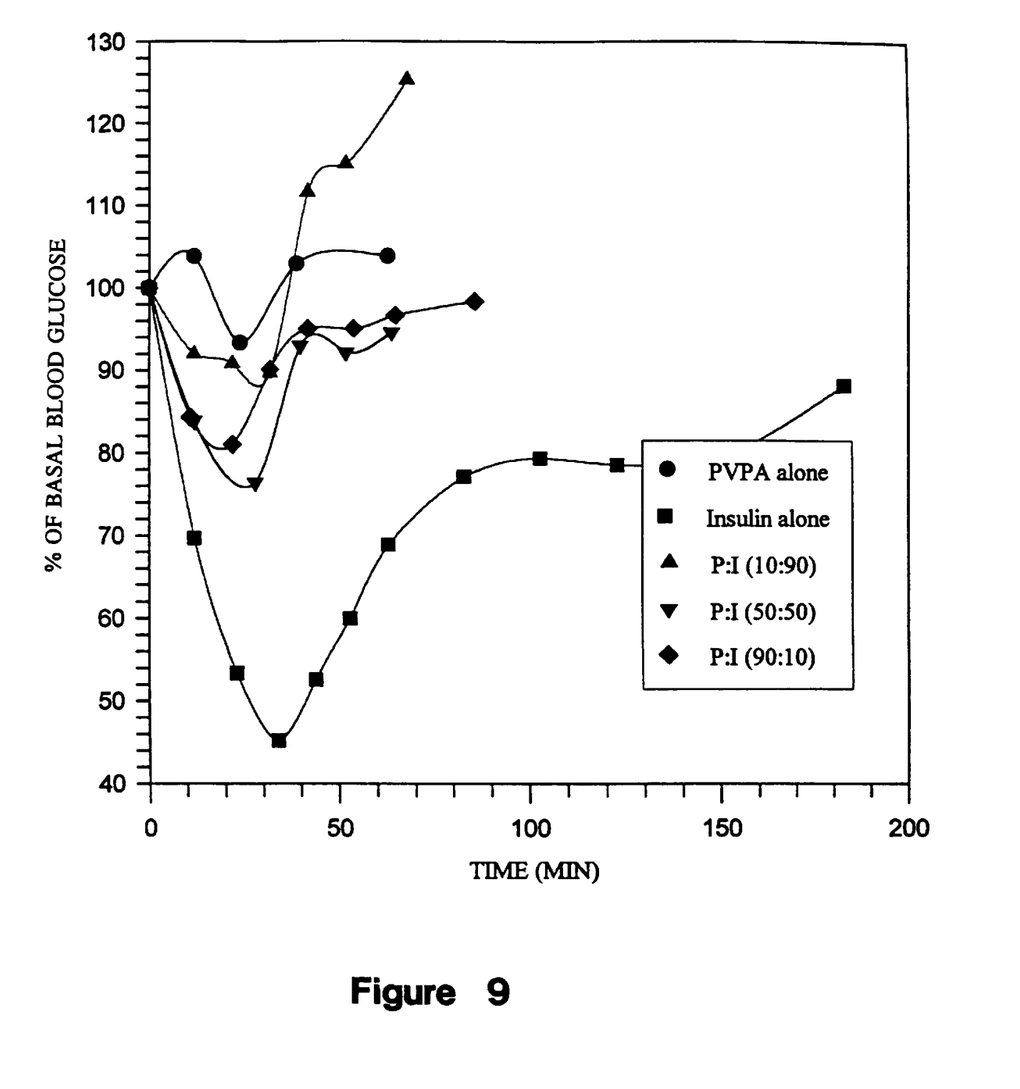
Figure 10:
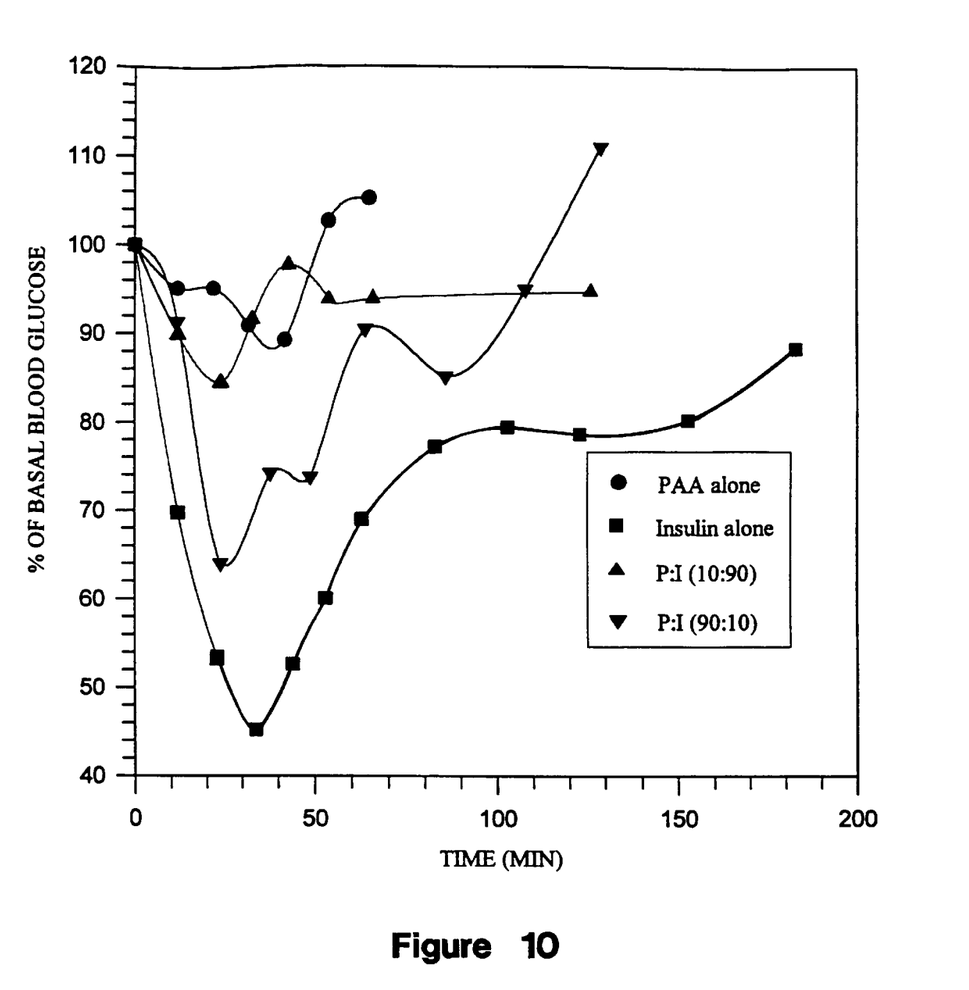
FIG. 10 are plots of % normal blood glucose vs. time for male rabbits administered either uncomplexed insulin or a macromolecular drug complex containing insulin and polyacrylic acid.

The macromolecular drug complexes, as shown in FIGS. 8–10, are capable of reducing serum glucose levels, but not as greatly as uncomplexed insulin. The macromolecular complexes containing processed insulin, as shown in FIG. 8, which were subjected to low levels of shear, reduced the serum glucose levels to a lesser extent than macromolecular complexes containing native insulin. The reduction in glucose levels achieved by uncomplexed insulin, however, can be attained by simply increasing the dose of the macromolecular insulin complex. Such dosage adjustments are well known and long practiced in the treatment of diabetics.

The results in FIGS. 8 and 9 show that the macromolecular complexes remain intact and do not dissociate immediately after intravenous administration. It also has been shown that the efficacy of insulin can be altered by formulating insulin as a macromolecular complex with polyvinylphosphonic acid. Furthermore, FIGS. 8 and 9 show that a 50:50 insulin-polymer weight ratio reduced blood glucose more effectively than a 90:10 and a 10:90 insulin-polymer weight ratio.

FIG. 10 shows that a macromolecular drug complex containing insulin and polyacrylic acid (PAA) likewise reduces blood glucose levels in vivo. Therefore, polyacrylic acid also can be used as the polymer to prepare a macromolecular drug complex, and to effectively deliver insulin.

During these tests different weight ratios of insulin to polyvinylphosphonic acid were used to prepare the macromolecular drug complexes. In particular, various macromolecular drug complexes were prepared, then centrifuged, and the supernatant liquid was analyzed for the presence of insulin and polyvinylphosphonic acid. The results are summarized in Table 2. The data in Table 2 shows that to achieve optimum complexing the weight ratio of polymer (P) to insulin (I) is at least about 10:90 by weight. The ratio of P to I can be as high as about 90:10. A preferred weight ratio of P to I is about 10:90 to about 75:25. To achieve the full advantage of the present invention, the P to I ratio is about 12.5:87.5 to about 25:75 because, as shown in Table 2, the amount of insulin and polyvinylphosphonic acid in the supernatant liquid was negligible. Accordingly, essentially all of the insulin and polyvinylphosphonic acid were complexed in the macromolecular drug complex.

TABLE 2

% EXCESS POLYVINYLPHOSPHONIC ACID (PVPA) AND INSULIN IN SUPERNATANT USING VARIOUS WEIGHT RATIOS OF PVPA AND INSULIN

| Weight Ratio of P:I | % free PVPA in supernatant | % free Insulin in supernatant |
|---|---|---|
| 5:95 | 0.16 | 65 |
| 10:90 | 0.11 | 9.2 |
| 12.5:87.5 | 0.21 | 3.3 |
| 15:85 | 0.24 | 0 |
| 25:75 | 2 | 0 |
| 40:60 | 54.5 | 0 |
| 60:40 | 70.5 | 0 |

The solubility of the macromolecular polymer complex containing insulin also was measured under various conditions and compared to standard insulin. The results are summarized in Table 3.

TABLE 3

SOLUBILITY OF INSULIN AND MACROMOLECULAR INSULIN COMPLEX

| | Insulin | Macromolecular Insulin Complex |
|---|---|---|
| pH = 3 | Soluble | Insoluble |
| pH = 7 | Insoluble | Soluble |
| pH = 7; phosphate buffer | Insoluble | Soluble |

The data in Table 3 shows that the solubility of uncomplexed insulin compared to the macromolecular insulin complex is reversed when the pH is increased from 3 to 7. The macromolecular complex is insoluble at low pH, but is soluble at neutral pH. Furthermore, the macromolecular complex is soluble in neutral buffer, whereas uncomplexed insulin is not. These results indicate that the new macromolecular insulin complexes can be used in a composition suitable for the oral administration of insulin.

In particular, a water soluble macromolecular insulin complex can be formed by complexing insulin with a neutralized form of the polymer. The neutralized form of the polymer is prepared by adding a base to an aqueous solution the polymer. The base typically is an alkali metal hydroxide, like sodium hydroxide or potassium hydroxide. However, other physiologically acceptable alkalis can be used to neutralize the polymer.

When using a neutralized form of the acid to form the macromolecular drug complex, the complex does not precipitate from solution after formation, but remains in solution. This soluble form of the macromolecular drug complex is suitable for administration by injection.

Another important embodiment of the present invention is a solid macromolecular insulin complex that can be used to administer insulin orally. A solid macromolecular complex is formed by complexing insulin with the free acid form of the polymer. In particular, an insulin solution is combined with an aqueous solution of the acid form of the polymer, and a precipitate forms. This precipitate, i.e., the macromolecular insulin complex, is insoluble in aqueous media at an acidic pH.

The water insolubility of the macromolecular insulin complex at an acidic pH makes the solid macromolecular insulin complex available for oral administration. Insulin has not been administered orally because the low pH of the stomach alters the insulin and makes the insulin unavailable to treat diabetes. However, the solid macromolecular insulin complexes are water insoluble at an acidic pH, and therfore the insulin, in a complexed form, is protected from stomach acids. After exiting the stomach and entering the gastrointestinal tract, the alkaline nature of the gastrointestinal tract neutralizes the acid moieties of the polymer, and the macromolecular complex becomes water soluble. The insulin then is available for adsorption by the individual to treat diabetes. The solid macromolecular insulin complexes therefore can be formulated, with suitable excipients that are well known to persons skilled in the art, to provide a powdered, solid composition that can be administered orally to treat diabetes.

The present invention therefore discloses a novel drug delivery system for the oral, parenteral, sublingual, transdermal, conjunctival, intraocular, intranasal, aural, intrarespiratory, rectal, vaginal, or urethral delivery of therapeutic agents. The drug delivery system comprises a macromolecular drug complex containing a polymer having a plurality of acid moieties and a therapeutic agent, including, but not limited to peptides, proteins, antibacterials, antifungals, antineoplastics, antiprotozoals, antiarthritics, and antiinflammatory agents. The polymers can be naturally occurring or synthetic, and are commercially available or can be readily synthesized.

In addition, although the present disclosure is particularly directed to the preparation of a macromolecular insulin complex, persons skilled in the art can apply this technology to a variety of therapeutic agents capable of complexing with a polymer having a plurality of acid moeities. The complexes are prepared by simply admixing the polymer, either in the free acid or neutralized form, with the therapeutic agent in an aqueous medium. The specific physicochemical properties of the resulting macromolecular complex can be adjusted by a judicious selection of the polymer and the $M_w$ of the polymer, by the number and type of acid moieties on the polymer, by the weight ratio of drug to polymer in the macromolecular complex, and by the number and type of polymer crosslinks.

Therefore, many modifications and variations of the invention as hereinbefore set forth can be made without departing from the spirit and scope thereof, and only such limitations should be imposed as are indicated by the appended claims.

What is claimed is:

1. A macromolecular drug complex comprising:
   (a) a drug having at least one quaternary ammonium nitrogen atom; and
   (b) a polymer having a plurality of acid moieties and a weight average molecular weight of about 2,000 to about 12,000, wherein the acid moieties of the polymer are selected from the group consisting of carboxyl, phosphate, phosphonate, sulfate, sulfonate, phenolic, and mixtures thereof, for noncovalent complexing with the quaternary ammonium nitrogen atom of the drug, wherein the complex is water-insoluble at an acidic pH and has a weight ratio of the drug to the polymer in the complex is about 10:90 to about 90:10, and wherein the formation of the macromolecular drug complex is confirmed by the CF-MALLS technique.

2. The complex of claim 1 wherein the drug is a polypeptide or a protein.

3. The complex of claim 1 wherein the drug is selected from the group consisting of insulin, tereofenamate, proglumetacin, tiaramide, apazone, benzpiperylon, pipebuzone, ramifenazone, methotrexate, isoniazid, polymyxin, bacitracin, tuberactionomycin, ethroyomycin, penicillamine, chloroquine phosphate, glucosamine, hydroxychloroquine, glucagon, cyclophosphamide, interferon α, interferon β, interferon γ, vincristine, and vinblastine.

4. The complex of claim 1 wherein the drug is selected from the group consisting of insulin, methotrexate, polymyxin, bacitracin, tuberactionomycin, chloroquine phosphate, glucagon, interferon α, interferon β, and interferon γ.

5. The complex of claim 1 wherein the drug is insulin.

6. The complex of claim 1 wherein the polymer comprises about 25% to 100%, by weight of the polymer, of a monomer having an acid moiety.

7. The complex of claim 1 wherein the polymer is lightly-crosslinked.

8. The complex of claim 1 wherein the naturally-occurring polymer is selected from the group consisting of heparin, dermatan sulfate, chondroitin sulfate, keratan sulfate, heparan sulfate, hyaluronic acid, carrageenan, and mixtures thereof.

9. The complex of claim 1 wherein the polymer is a synthetic polymer.

10. The complex of claim 9 wherein the synthetic polymer is a homopolymer of an α, β-unsaturated carboxylic acid.

11. The complex of claim 9 wherein the synthetic polymer is a copolymer of an α, β-unsaturated carboxylic acid and a comonomer.

12. The complex of claim 11 wherein the comonomer is selected from the group consisting of ethylene, propylene, a $C_{4-5}$ alkene, a $C_1$–$C_{12}$ ester of an α, β-unsaturated carboxylic acid ester, vinyl propionate, acrylamide, methacrylamide, styrene, α-methyl toluene, vinyl toluene, vinylpyrrolidone, vinyl alcohol, vinyl acetate, a vinyl alkyl ether, and mixtures thereof.

13. The complex of claim 9 wherein the α, β-unsaturated carboxylic acid is selected from the group consisting of acrylic acid, methacrylic acid, maleic acid, fumaric acid, itaconic acid, mesaconic acid, citraconic acid, vinylphosphonic acid, and mixtures thereof.

14. The complex of claim 9 wherein the polymer comprises sulfated aromatic monomers or sulfonated aromatic monomers.

15. The complex of claim 1 wherein the polymer is selected from the group consisting of polyacrylic acid, polyvinylphosphonic acid, polyvinylsulfonic acid, polystyrenesulfonic acid, polymaleic acid, polymethacrylic acid, polyvinylsulfuric acid, poly(2-methacroyloxyethane-1-sulfonic acid, poly(4-vinylbenzoic acid), poly(3-(vinyloxy) propane-1-sulfonic acid), poly(3-(vinyloxy)propane-1-sulfonic acid), poly(3-methacryloxypropane-1-sulfonic acid), polymethacrylic acid, poly(4-vinylphenol), poly (4-vinylphenyl sulfuric acid), poly(N-vinylsuccinamidic acid), and mixtures thereof.

16. The complex of claim 1 wherein the polymer is selected from the group consisting of polyvinylphosphonic acid and polyacrylic acid.

17. The complex of claim 1 wherein the weight ratio of the drug to the polymer is about 10:90 to about 75:25.

18. The complex of claim 1 wherien the weight ratio of the drug to the polymer is about 12.5:87.5 to about 50:50.

19. The complex of claim 1 wherein the polymer is in a free acid form.

20. The complex of claim 1 wherein the polymer is in a salt form.

21. The complex of claim 1 wherein the drug complex is water soluble at pH 7 or greater.

22. The complex of claim 1 wherein the drug is insulin and the polymer is selected from the group consisting of polyacrylic acid, polyvinylphosphonic acid, and mixtures thereof.

23. The complex of claim 22 wherein the polymer has a weight average molecular weight of about 4,000 to about 12,000.

24. A drug composition comprising:
(a) a macromolecular drug complex comprising
    (i) a drug having at least one quaternary ammonium nitrogen atom; and
    (ii) a polymer having a plurality of acid moieties and a weight average molecular weight of about 2,000 to about 12,000, wherein the acid moieties of the polymer are selected from the group consisting of carboxyl, phosphate, phosphonate, sulfate, sulfonate, phenolic, and mixtures thereof, for noncovalent complexing with the quaternary ammonium nitrogen atom of the drug,
wherein the complex is water-insoluble at an acidic pH and has a weight ratio of the drug to the polymer in the complex is about 10:90 to about 90:10, and wherein the formation of the macromolecular drug complex is confirmed by the CF-MALLS technique.

25. The composition of claim 24 wherein the macromolecular drug complex is water soluble at pH about 7 or greater and the carrier comprises water.

26. The composition of claim 24 wherein the carrier comprises a solid excipient, and the composition is in a solid form.

27. A method of treating diabetes comprising administering a therapeutically-effective amount of a macromolecular insulin complex to a diabetic, said molecular insulin complex comprising: (a) insulin, and (b) a polymer having a plurality of acid moieties and a weight average molecular weight of about 2,000 to about 12.000, wherein the acid moieties of the polymer are selected from the group consisting of carboxyl, phosphate, phosphonate, sulfate, sulfonate, phenolic, and mixtures thereof, for noncovalent complexing with the quaternary ammonium nitrogen atom of the drug,
wherein the complex is water-insoluble at an acidic pH and has a weight ratio of the insulin to the polymer in the complex is about 10:90 to about 90:10, and wherein the formation of the macromolecular drug complex is confirmed by the CF-MALLS technique.

28. The method of claim 27 wherein the macromolecular insulin complex is water soluble at about pH 7 or greater and is administered intravenously.

29. The method of claim 27 wherein is administered orally.

30. A method of treating diabetes and vascular complications associated with diabetes comprising: (a) insulin, and (b) a polymer having a plurality of acid moieties and a weight average molecular weight of about 2.000 to about 12,000, wherein the acid moieties of the polymer are selected from the group consisting of carboxyl, phosphate, phosphonate, sulfate, sulfonate, phenolic, and mixtures thereof, for noncovalent complexing with the quaternary ammonium nitrogen atom of the drug,
wherein the complex is water-insoluble at an acidic pH and has a weight ratio of the insulin to the polymer in the complex is about 10:90 to about 90:10, and wherein the formation of the macromolecular drug complex is confirmed by the CF-MALLS technique.

31. A method of treating a disease and complications associated with the disease comprising administering a therapeutically-effective amount of a macromolecular drug complex comprising: (a) a therapeutic drug for the disease and (b) a polymer having a plurality of acid moieties and a weight average molecular weight of about 2,000 to about 12,000, wherein the acid moieties of the polymer are selected from the group consisting of carboxyl, phosphate, phosphonate, sulfate, sulfonate, phenolic, and mixtures thereof, for noncovalent complexing with the quaternary ammonium nitrogen atom of the drug,
wherein the complex is water-insoluble at an acidic pH and has a weight ratio of the insulin to the polymer in the complex is about 10:90 to about 90:10, and wherein the formation of the macromolecular drug complex is confirmed by the CF-MALLS technique.

* * * * *